United States Patent [19]

Engelhardt et al.

[11] Patent Number: 5,360,452
[45] Date of Patent: Nov. 1, 1994

[54] ENHANCED FIXATION SYSTEM FOR A PROSTHETIC IMPLANT

[75] Inventors: John Engelhardt; Jon Serbousek, both of Warsaw, Ind.

[73] Assignee: DePuy Inc., Warsaw, Ind.

[21] Appl. No.: 163,597

[22] Filed: Dec. 6, 1993

Related U.S. Application Data

[63] Continuation of Ser. No. 954,684, Sep. 30, 1992, abandoned, which is a continuation of Ser. No. 702,744, May 20, 1991, abandoned.

[51] Int. Cl.⁵ .......................... A61F 2/32; A61F 2/36; A61F 2/30; A61F 2/28
[52] U.S. Cl. ........................................ 623/22; 623/23; 623/18; 623/16; 606/71; 606/72; 606/73
[58] Field of Search ................ 623/16, 18, 22, 23; 606/71, 72, 73

[56] References Cited

U.S. PATENT DOCUMENTS

| | | |
|---|---|---|
| Re. 28,895 | 7/1976 | Noiles . |
| 3,605,123 | 9/1971 | Hahn ............................ 623/16 |
| 3,641,590 | 2/1972 | Michele . |
| 3,685,058 | 8/1972 | Tronzo . |
| 3,855,638 | 12/1974 | Pillar ............................ 128/92 X |
| 3,903,549 | 9/1975 | Deyerle . |
| 3,906,550 | 9/1975 | Rostoker et al. . |
| 4,011,602 | 3/1977 | Rybicki et al. .................. 623/16 |
| 4,177,524 | 12/1979 | Grell et al. ..................... 606/73 |
| 4,380,090 | 4/1983 | Ramos . |
| 4,563,778 | 1/1986 | Roche et al. . |
| 4,566,138 | 1/1986 | Lewis et al. . |
| 4,650,491 | 3/1987 | Parchinski ...................... 623/22 |
| 4,711,234 | 12/1987 | Vives et al. .................. 623/16 X |
| 4,769,041 | 9/1988 | Morscher . |
| 4,792,337 | 12/1988 | Muller . |
| 4,854,496 | 8/1989 | Bugle ........................ 623/22 X |
| 4,871,368 | 10/1989 | Wagner ......................... 623/22 |
| 4,936,856 | 6/1990 | Keller ......................... 623/22 |
| 4,955,917 | 9/1990 | Karpf .......................... 623/22 |
| 4,990,161 | 2/1991 | Kampner ....................... 623/16 |
| 5,021,062 | 6/1991 | Adrey et al. ................... 623/22 |
| 5,053,036 | 10/1991 | Perren et al. ............... 606/71 X |
| 5,084,050 | 1/1992 | Draenert .................... 606/73 X |
| 5,085,660 | 2/1992 | Lin .......................... 606/69 X |
| 5,098,434 | 3/1992 | Serbouser .................. 606/66 X |

FOREIGN PATENT DOCUMENTS

| | | |
|---|---|---|
| 2301810 | 7/1973 | European Pat. Off. . |
| 0123514 | 10/1984 | European Pat. Off. . |
| 0285756 | 12/1988 | European Pat. Off. . |
| 0295912 | 12/1988 | European Pat. Off. . |

Primary Examiner—Randall L. Green
Assistant Examiner—Dinh X. Nguyen
Attorney, Agent, or Firm—Perman & Green

[57] ABSTRACT

A system is disclosed for the fixation of a component of an artificial joint for replacing a damaged natural joint. A cup-shaped socket member is formed with a plurality of radially directed through bores, each being threaded adjacent an outer hemispherical surface and each being tapered adjacent an inner hemispherical surface to define a seating surface. A fastener with an elongated shank secures the socket member to a bone and is received through each through bore. The fastener extends between a head at a first end and a tip at a second end. Mounting threads on the shank intermediate the first and second ends are threadedly engaged with the threads in the through bore and a tapered outer surface extending between the mounting threads and the second end is matingly engaged with the seating surface in the bore. The shank between the mounting threads and the tip end may be smooth, or porous coated to encourage bone ingrowth fixation, or have cancellous threads thereon for threaded engagement with the bone, or different combinations of these expedients may be used.

17 Claims, 1 Drawing Sheet

ENHANCED FIXATION SYSTEM FOR A PROSTHETIC IMPLANT

This is a continuation of copending application Ser. No. 07/954,684 filed on Sep. 30, 1992, which is a continuation of copending application Ser. No. 07/702,744 filed on May 20, 1991, both now abandoned.

FIELD OF THE INVENTION

The present invention relates generally to prosthetic implants and more particularly to a system for the fixation of a prosthetic component to an underlying bone. A total hip replacement prosthesis is of particular concern and, in this regard, the mounting of the acetabular socket member to the cavity of an acetabulum.

DESCRIPTION OF THE PRIOR ART

Prior art cups have generally been of two types. First, cups may be conventional hemispherical cups with or without a porous coating on their outer surface. Second, cups are available which may include pre-attached spikes which are necessarily parallel to the axis of implantation of the cup.

An example of a prosthetic socket utilizing parallel spikes aligned in the direction of its implantation into a receiving acetabular cavity is presented in U.S. Pat. No. 3,685,058. Improvements to such a construction, however, are typically disclosed in U.S. Pat. Nos. 3,641,590 and 4,792,337. In each of these patents, the acetabular socket member is first properly positioned in the cavity of the acetabulum, and thereafter, a suitable pin, nail, or screw is driven through a bore in the socket member and into the acetabulum. As disclosed in each of these patents, the fastener member is angularly disposed relative to a vector indicative of the direction of movement of the socket member toward the bone as it is being implanted. Such an orientation of the fastener serves to increase the difficulty of unintended withdrawal of the socket member from the acetabulum.

However, even with these noted improvements, problems remain. Specifically, when screws were used, as disclosed in the '337 patent, they tended to loosen soon after they were mated with the bone. Additionally, when either screws were used as in the '337 patent or pins or nails as in the '590 patent, they tended to move relative to the socket member, thereby producing fretting in the region where the fasteners mate with the holes in the cup. Debris undesirably forms as a result of the fretting and this, in turn, can lead to trauma to the patient and, eventually, to failure of the prosthesis in an extreme situation.

It was with knowledge of the foregoing constructions that the present invention has been conceived and now reduced to practice.

SUMMARY OF THE INVENTION

According to the present invention, a system is disclosed for the fixation of a component of an artificial joint for replacing a damaged natural joint. A cup-shaped socket member is formed with a plurality of radially directed through bores, each being threaded adjacent an outer hemispherical surface and each being tapered adjacent an inner hemispherical surface to define a seating surface. A fastener with an elongated shank secures the socket member to a bone and is received through each through bore. The fastener extends between a head at a first end and a tip at a second end. Mounting threads on the shank intermediate the first and second ends are threadedly engaged with the thread in the through bore and a tapered outer surface extending between the mounting threads and the second end is matingly engaged with the seating surface in the bore. The shank between the mounting threads and the tip end may be smooth, or porous coated to encourage bone ingrowth fixation, or have cancellous threads thereon for threaded engagement with the bone, or different combinations of these expedients may be used.

Relative movement between the fastener and the socket member is avoided by the present invention, and the oblique positioning of the fastener assures a long lasting implant.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and, together with the description, serve to explain the principles of the invention in general terms. Like numerals refer to like parts throughout the disclosure.

DETAILED DESCRIPTION OF THE PREFERRED EMBODIMENTS

Figure 1:
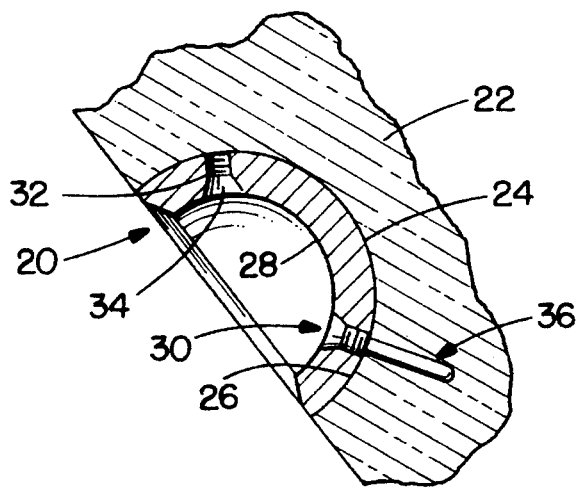
FIG. 1 is a cross section view in elevation illustrating a prosthetic implant embodying the fixation system of the present invention.
Figure 2:
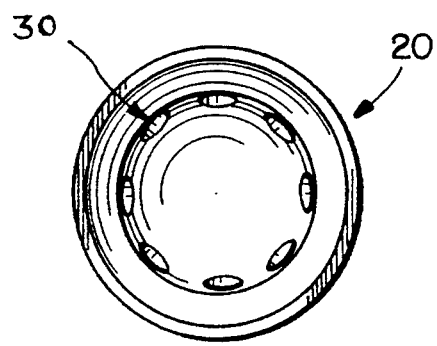
FIG. 2 is a plan view of a component of the fixation system illustrated in FIG. 1.

Turn now to the drawings and, initially, to FIGS. 1 and 2 which generally illustrate a fixation system embodying the present invention. Specifically, a generally hemispherical cup-shaped socket member 20 is shown implanted in a receiving bone 22. The socket member 20 has an outer curved surface 24 for contiguous mating reception with a similar shaped cavity 26 in the bone 22. By way of example, the bone 22 may be an acetabulum, the cavity 26 an acetabular cavity, and the socket member 20 an acetabular component of a hip prosthesis. The socket member 20 also has an inner curved surface 28 which is generally parallel to and spaced from the outer surface 24. The inner surface 28 normally serves to receive a polyethylene liner (not shown) in a known manner for supporting reception of a mating ball-shaped member attached to a second bone (not shown).

The socket member 20 has at least one generally radially directed mounting bore 30 extending between the inner and outer surfaces 24, 28. As seen in FIG. 1, one portion of the bore proximate the outer surface 24 is threaded as at 32 and another portion of the bore proximate the inner surface 28 is tapered to define a conically shaped seating surface 34. The seating surface 34 flares inwardly such that the bore 30 has a major diameter in the plane in the inner surface 28 and a minor diameter intermediate the inner and outer surfaces 28, 24, respectively.

A fixation fastener of a unique design is utilized in combination with the socket member 20. One embodiment of such a fixation fastener is indicated at 36 in FIG. 3A. As seen in FIG. 1, the fastener 36 is intended for reception through the mounting bore 30 and into the bone 22. The fastener 36 includes a head 38, an elongated shank 40 integral with, and extending away from, the head and mounting threads 42 adjacent the head 38. The threads 42 are machine screw threads. The head 38 of the fastener 36 has an operating end 44 (FIG. 3A) and an outer tapered surface 46 extending between the operating end and the mounting threads 42. The diameter of the head 38 is greater at the operating end 44 than at the mounting threads 42.

Figures 4A, 4B, 4C:
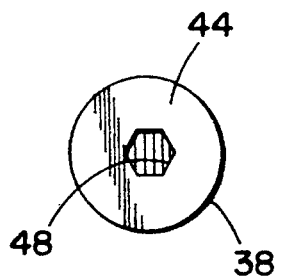
FIGS. 4A, 4B, and 4C are top plan views illustrating typical recesses in the heads thereof for reception by suitable mounting tools.

As seen in FIG. 1, when the fastener 36 is used to affix the socket member 20 to the bone 22, it is advanced through the mounting bore 30 and its shank is advanced into the bone 22. The fastener 36 continues to be advanced through the mounting bore 30 until the mounting threads 42 become threadedly engaged with the threads 32 in the bore 30 of the socket member 20. An appropriate tool is used to advance the fastener 36 into mounting position, then to tighten the fastener by way of the mutually engageable threads 42 and 32. Any one of a variety of tools can be used for this purpose. For example, in FIG. 4A, the operating end 44 of the fastener is shown provided with a hexagonal recess 48 for reception by a suitable Allen wrench. In FIG. 4B, a modified operating end 44A may be provided with a recess 50 in the shape of a cross suitable for receiving a Phillips type screwdriver. Still another variation is depicted in FIG. 4C in which a modified operating end 44B is provided with an elongated, or slotted, recess 52 shaped to receive the blade end of a conventional screwdriver. It will be appreciated that a variety of other types of tools can also be accommodated by the fastener 36. When the fastener 36 is fully tightened so as to be in a final position fixedly mounting the socket member to the bone 22, the tapered surface 46 is matingly engaged with the seating surface 34 and the operating end 44 is substantially flush with the inner surface 28 or slightly depressed therefrom.

A plurality of fasteners 36 are preferably employed as seen in FIG. 2 at spaced circumferential locations. It is also preferable that the longitudinal axes of the fasteners 36, when in their final positions fixedly mounting the socket member 20 to the bone 22, are angularly disposed relative to the direction of advancement of the socket member toward the first bone as it is being implanted. In this manner, the possibility of unintended withdrawal of the socket member 20 from the bone 22 is minimized.

It will also be appreciated that by reason of a fact that the mating threads 42, 32 firmly fasten the fastener 36 to the socket member 20, relative movement between the fastener and the socket member is eliminated. This construction, in turn, eliminates fretting between those components and the resultant debris which can traumatize the patient and eventually impair the success of the implant.

Figures 3A, 3B, 3C, 3D:
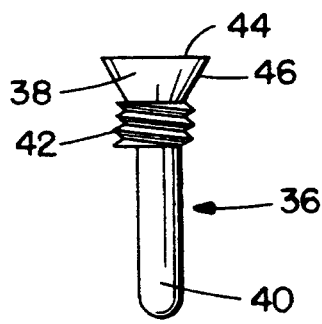
FIGS. 3A, 3B, 3C, 3D, and 3E are side elevation views illustrating novel fasteners for use in conjunction with the fixation system of the invention.

Another embodiment of the novel fastener of the invention is indicated at 54 in FIG. 3B. The fastener 54 may be generally similar to the fastener 36 but with the further provision of a porous surface 56 on its stem for bone ingrowth fixation. An excellent example of such a surface results from application of the proprietary porous metal coating of DePuy Division of Boehringer Mannheim Corporation provided under the trademark "POROCOAT". Representative patents in this field include U.S. Pat. Nos. 3,605,123 to Hahn, 3,855,638 to Pilljar, 4,536,894 to Galante et al, and 4,854,496 to Bugle. With such a surface on the fastener in the region contiguous to bone 22, long term stabilization is even further enhanced over that of the fastener 36 with the unmodified shank 40. Of course, it is often desirable to provide such a porous coating on the outer surface 24 of the socket member 20, as well.

It was previously mentioned that the angle of taper of the tapered surface 46 is preferably substantially similar to that of the seating surface 34. Additionally, if desired, the angle of taper may be chosen substantially small so as to be a locking taper. For example, as seen in FIG. 3C, the tapered surface 46 and the longitudinal axis of the fastener 58 may have an included angle of less than approximately six degrees. As a result, upon tightening of the fastener 36, the fastener 36 becomes locked together with the socket member 20 when the tapered surface 46 is advanced into firm engagement with the seating surface 34. In this manner, both the mounting threads 42 and the tapered surface 46 on the fastener 36 are effective to prevent undesired relative movement between the fastener and the socket member.

Still another embodiment of the invention is generally indicated at 62 as seen in FIG. 3D. In this instance, the fastener 62 may be generally similar to the fastener 36 but with the addition of cancellous screw threads formed along at least part of the length of the shank beneath the mounting threads 42. In one instance, the pitch of the cancellous screw threads 64 may be similar to the pitch of the mounting threads 42 such that the former advance through the bone at the identical rate at which the latter advance into the threads 32 of the socket member 20. While this is a preferred construction, it may also be that the pitch of the cancellous screw threads 64 is slightly greater than that of the mounting threads 42. In this instance, the cancellous threads would cause some bone to build up around the base of the threads 64, especially during the last few turns of the fastener 62 which may further improve stability of the resulting construction.

Figure 3E:
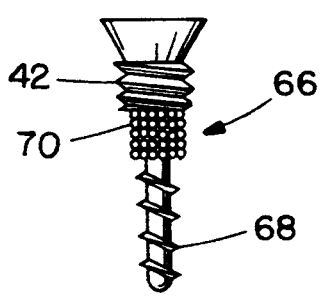

Yet another embodiment of the invention is indicated at 66 in FIG. 3E which may be generally similar to the fastener 36 but with cancellous screw threads 68 at a distal end of the shank and a porous surface 70 at a proximal end of the shank intermediate the mounting threads 42 and the cancellous screw threads 68. The fastener 66 thereby represents a compromised attempt to utilize optimally the benefits of all of the teachings of the present invention.

While preferred embodiments of the invention have been disclosed in detail, it should be understood by those skilled in the art that various other modifications may be made to the illustrated embodiments without departing from the scope of the invention as described in the specification and defined in the appended claims.

We claim:

1. A system for the fixation of a component of an artificial joint for replacing a damaged natural joint comprising:

a cup-shaped socket member generally hemispherical in shape, having an outer curved surface for contiguous mating reception with a similarly shaped cavity in a first bone and an inner curved surface generally parallel to and spaced from said outer surface for supporting reception therein of a mating ball-shaped member attached to a second bone, said socket member having at least one mounting bore extending between said inner and outer surfaces and having a longitudinal axis, one portion of the bore proximate said outer surface being threaded, another portion of the bore proximate said inner surface being uniformly tapered relative to the longitudinal axis and having an included angle of less than six degrees and having a major diameter at said inner surface and a minor diameter intermediate said outer and inner surfaces thereby defining a seating surface; and a one piece fixation fastener for reception through the mounting bore and into the first bone, said fastener having a longitudinal axis and extending between first and second ends and including:

a head;

an elongated shank integral with and extending away from said head;

mounting threads on said fastener adjacent said head;

said head having an operating end and a locking surface being uniformly tapered relative to the longitudinal axis and having an included angle of less than six degrees, and extending between said operating end and said mounting threads and having a diameter at said operating end greater than at said mounting threads;

said mounting threads on said fastener being threadedly engaged with said threads in the bore and said tapered locking surface on said fastener being matingly engaged with said seating surface in the bore when said fastener is in a final position fixedly mounting said socket member to the first bone, said seating surface of said socket member and said locking surface of said fixation fastener having a mutual angular divergence sufficient to cause a locked condition when engaged whereby both a torsional frictional load is imparted between said locking surface and said seating surface of said socket member and a tensile load is imparted between said mounting threads and said locking surface, said torsional and tensile loads being confined to a region defined by said outer curved surface and Said inner curved surface to prevent loosening of said fastener from said socket member.

2. A fixation system as set forth in claim 1 wherein the longitudinal axis of said fastener, when in the final position fixedly mounting said socket member to the first bone, is angularly disposed relative to the direction of advancement of said socket member toward the first bone for implantation therewith.

3. A fixation system as set forth in claim 1 including means on said head for advancing said fastener toward the final position.

4. A fixation system as set forth in claim 3 wherein said advancing means includes a shaped recess aligned with the longitudinal axis for reception therein of a tool for advancing said fastener toward the final position.

5. A fixation system as set forth in claim 1 wherein said outer surface of said shank between said mounting threads and said first end has a porous medium thereon for encouraging bone ingrowth fixation.

6. A fixation system as set forth in claim 1 wherein a first length of said outer surface of said shank between said mounting threads and said first end has a porous medium thereon for encouraging bone ingrowth fixation; and wherein a second length of said outer surface of said shank adjacent said first length is relatively smooth.

7. A fixation system as set forth in claim 1 wherein said shank includes cancellous screw threads formed along at least part of the length thereof for threaded engagement with the first bone.

8. A fixation system as set forth in claim 1 wherein a first length of said outer surface of said shank between said mounting threads and said first end has a porous medium thereon for encouraging bone ingrowth fixation; and wherein a second length of said shank adjacent said first length includes cancellous screw threads thereon for threaded engagement with the first bone.

9. A fixation system as set forth in claim 1 wherein the first bone is an acetabulum and said socket member is an acetabular cup.

10. A fixation system as set forth in claim 1 wherein said head includes coupling means on said operating end engageable by a tool for selectively rotating said fastener to draw said tapered surface into engagement with said seating surface and to advance said fastener into the first bone.

11. A fixation system as set forth in claim 1 wherein said fastener is composed of a material selected from the group consisting of titanium and alloys thereof, cobalt chromium and alloys thereof, stainless steel and alloys thereof, and composite materials.

12. A fixation system as set forth in claim 10 wherein said coupling means includes a formation in said head for mating reception by the terminal portion of a tool.

13. A fixation system as set forth in claim 1 wherein each mounting bore in said socket member is generally radially directed.

14. A system for the fixation of a component of an artificial joint for replacing a damaged natural joint comprising:

a cup-shaped socket member generally hemispherical in shape, having an outer curved surface for contiguous mating reception with a similarly shaped cavity in a first bone and an inner curved surface generally parallel to and spaced from said outer surface for supporting reception therein of a mating ball-shaped member attached to a second bone, said socket member having at least one mounting bore extending between said inner and outer surfaces and having a longitudinal axis, one portion of the bore proximate said outer surface being threaded, another portion of the bore proximate said inner surface being uniformly tapered relative to the longitudinal axis and having an included angle of less than six degrees and having a major diameter at said inner surface and a minor diameter intermediate said outer and inner surfaces thereby defining a seating surface; and a one piece fixation fastener for reception through the mounting bore and into the first bone, said fastener having a longitudinal axis and extending between first and second ends and including:

a head;

an elongated shank integral with and extending away from said head;

mounting threads on said fastener adjacent said head;

said head having an operating end and a locking surface being uniformly tapered relative to the longitudinal axis and having an included angle of less than six degrees, and extending between said operating end and said mounting threads and having a diameter at said operating end greater than at said mounting threads;

said mounting threads on said fastener being threadedly engaged with said threads in the bore and said tapered locking surface on said fastener being matingly engaged with said seating surface in the bore when said fastener is in a final position fixedly mounting said socket member to the first bone, said seating surface of said socket member and said locking surface of said fixation member having a mutual angular divergence sufficient to cause a locked condition when engaged, said outer surface of said shank between said mounting threads and said first end having a porous medium thereon for encouraging bone ingrowth fixation whereby both a torsional frictional load is imparted between said locking surface and seating surface of said socket member and a tensile load is imparted between said mounting threads and said locking surface, said torsional and tensile loads being confined to a region defined by said outer curved surface and said inner curved surface to prevent loosening of said fastener from said socket member.

15. In a system for the fixation to bone of a component of an artificial joint for replacing a damaged natural joint, a one piece fixation fastener for reception through a mounting bore of the component and into the bone, said fastener having a longitudinal axis comprising:

a head;

an elongated shank integral with and extending away from said head;

mounting threads on said fastener adjacent said head;

said head having an operating end and a locking surface being uniformly tapered relative to the longitudinal axis and having an included angle of less than six degrees, and extending between said operating end and said mounting threads and having a diameter at said operating end greater than at said mounting threads;

said mounting threads on said fastener being threadedly engageable with threads in the mounting bore of the component and said locking surface on said fastener being matingly engageable with a seating surface in the mounting bore of the component when said fastener is in a final position fixedly mounting the component to the bone, the seating surface in the mounting bore of the component and said locking surface of said fastener having a mutual angular divergence sufficient to cause a locked condition when engaged whereby both a torsional frictional load is imparted between said locking surface and the seating surface of the component and a tensile load is imparted between said mounting threads and said locking surface, said torsional and tensile loads being confined to a region defined by the mounting bore of the component to prevent Loosening of said fastener from the component.

16. In a system for the fixation to bone of a component of an artificial joint for replacing a damaged natural joint, a one piece fixation fastener for reception through a mounting bore of the component and into the bone, said fastener having a longitudinal axis and extending between first and second ends and comprising:

a head;

an elongated shank integral with and extending away from said head;

mounting threads on said fastener adjacent said head;

said head having an operating end and a locking surface being uniformly tapered relative to the longitudinal axis and having an included angle of less than six degrees, and extending between said operating end and said mounting threads and having a diameter at said operating end greater than at said mounting threads;

said mounting threads on said fastener being threadedly engageable with threads in the mounting bore of the component and said locking surface on said fastener being matingly engageable with a seating surface in the mounting bore of the component when said fastener is in a final position fixedly mounting the component to the bone, the seating surface in the mounting bore of the component and said locking surface of said fastener having a mutual angular divergence sufficient to cause a locked condition when engaged, said outer surface of said shank between said mounting threads and extending toward said first end having a porous medium thereon for encouraging bone ingrowth fixation whereby both a torsional frictional load is imparted between said locking surface and the seating surface of the component and a tensile load is imparted between said mounting threads and said locking surface, said torsional and tensile loads being confined to a region defined by the mounting bore of the component to prevent loosening of said fastener from the component.

17. A fixation fastener as set forth in claim 16 wherein a length of said shank intermediate said outer surface with said porous medium thereon and said first end including cancellous screw threads thereon for threaded engagement with the bone.

* * * * *